(12) United States Patent
Barth et al.

(10) Patent No.: US 7,576,243 B2
(45) Date of Patent: Aug. 18, 2009

(54) PROCESS FOR PREPARING METHYL MERCAPTAN FROM DIALKYL SULPHIDES AND DIALKYL POLYSULPHIDES

(75) Inventors: Jan-Olaf Barth, Frankfurt (DE); Hubert Redlingshöfer, Münchsteinach (DE); Christoph Weckbecker, Gründau-Lieblos (DE); Klaus Huthmacher, Gelnhausen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 12/026,695

(22) Filed: Feb. 6, 2008

(65) Prior Publication Data
US 2008/0200730 A1 Aug. 21, 2008

(30) Foreign Application Priority Data
Feb. 15, 2007 (DE) .................... 10 2007 007 458

(51) Int. Cl.
*C07C 319/00* (2006.01)
(52) U.S. Cl. ........................................ 568/70
(58) Field of Classification Search ............. 568/70
See application file for complete search history.

(56) References Cited

U.S. PATENT DOCUMENTS

| 2,816,146 | A | | 12/1957 | Doumani |
| 2,831,031 | A | | 4/1958 | Binning et al. |
| 4,005,149 | A | | 1/1977 | Kubicek |
| 4,313,006 | A | * | 1/1982 | Hager ................. 568/70 |
| 4,396,778 | A | * | 8/1983 | Hager ................. 568/70 |
| 4,927,972 | A | * | 5/1990 | Arretz ................. 554/101 |
| 5,453,543 | A | * | 9/1995 | Gernon et al. ......... 568/70 |
| 5,493,058 | A | * | 2/1996 | Cadot et al. .......... 568/70 |
| 5,866,721 | A | | 2/1999 | Hofen et al. |

FOREIGN PATENT DOCUMENTS

| DE | 1193038 | 5/1965 |
| JP | 5246203 | 12/1977 |
| JP | 58159456 | 9/1983 |

OTHER PUBLICATIONS

Mashkina et al.; React. Kinet. Catal. Lett., vol. 70, No. 1, 183-189, 2000.
Koshelev et al.; React. Kinet. Catal., vol. 27, No. 2, 387-391 (1985).

* cited by examiner

*Primary Examiner*—Jafar Parsa
*Assistant Examiner*—Chukwuma O Nwaonicha
(74) *Attorney, Agent, or Firm*—Robert G. Weilacher; Smith, Gambrell & Russell, LLP

(57) ABSTRACT

A process for continuously preparing methyl mercaptan by reacting a reactant mixture which contains a dialkyl sulphide and a dialkyl polysulphide with hydrogen sulphide to give methyl mercaptan.

14 Claims, 3 Drawing Sheets

PROCESS FOR PREPARING METHYL MERCAPTAN FROM DIALKYL SULPHIDES AND DIALKYL POLYSULPHIDES

INTRODUCTION AND BACKGROUND

The invention relates to a process for preparing alkyl mercaptan by reacting a reactant mixture comprising dialkyl sulphides and/or dialkyl polysulphides and optionally dialkyl ethers with hydrogen sulphide over heterogeneous catalysts.

Methyl mercaptan is an industrially important intermediate for the synthesis of methionine and for the preparation of dimethyl sulphoxide and dimethyl sulphone. Methyl mercaptan is prepared predominantly from methanol and hydrogen sulphide by reaction over a catalyst consisting of an aluminium oxide support and transition metal oxides and basic promoters.

In the reaction of methanol with hydrogen sulphide, at the typical reaction temperatures and using an economically viable hydrogen sulphide excess, the reaction equilibrium is such that dimethyl sulphide is always formed as well as methyl mercaptan. In addition to thioether formation, the reaction to give polysulphides (e.g., dimethyl disulphide) is also observed. These compounds are removed in the course of workup of the product gas stream. When no further economically viable utilization of these components is possible, the by-products are typically disposed of, for example by incineration or reaction with alkalis. This procedure lowers the overall selectivity of the preparation process for methyl mercaptan and hence the economic viability of the process. In this context, one alternative is the recycling of the sulphides or polysulphides into the process. When the sulphide level, according to U.S. Pat. No. 2,816,146, is kept sufficiently high by a recycling, the new formation of mercaptans from alcohols or ethers is suppressed. The process has the serious disadvantage that large amounts of sulphides have to be separated, condensed and, on recycling into the circuit, evaporated again. For this purpose, large amounts of heat and cooling energies are required.

Typical catalysts which are used in industrial processes for producing methyl mercaptan from methanol and hydrogen sulphide exhibit high selectivities for the formation of methyl mercaptan and lead to a comparatively low evolution of dimethyl sulphide and dimethyl disulphide. A problem in this connection is that these compounds accumulate in the circuit when they are recycled into the process, since the catalysts used in the prior art can only poorly establish the equilibrium between methyl mercaptan and dimethyl sulphide. This means that, in each case, at most a quarter of the undesired newly formed sulphide is converted in the case of recycling into the circuit.

As shown by DE-C 1193038, it is also possible to separate the sulphide and to convert it in a separate reaction step over a different catalyst to methyl mercaptan. However, it is necessary to select a high excess of hydrogen sulphide in order to achieve technically relevant conversions of dimethyl sulphide. DE-C 1193038 describes a process in which the sulphide formed, in an upstream reactor, together with the total amount of hydrogen sulphide required, is passed over a catalyst which efficiently establishes the reaction equilibrium between sulphide and mercaptan (precatalyst, e.g. $MoO_3/Al_2O_3$). The reaction products obtained are subsequently, after addition of methanol or dimethyl ether, conducted over a main catalyst ($K_2WO_4/Al_2O_3$) over which the alcohol or the ether reacts with as yet unconverted hydrogen sulphide to give methyl mercaptan.

As described in the above-mentioned patent application, the separation of reaction product and hydrogen sulphide in the case of use of large hydrogen sulphide excesses is, however, found to be difficult.

JP 58159456 relates to a methyl mercaptan process in which the hydrogen sulphide conducted in the circuit is mixed with fresh hydrogen sulphide, and the overall $H_2S$ stream is subsequently divided between a methyl mercaptan reactor and a DMS cleavage reactor. Upstream of the methyl mercaptan reactor, one $H_2S$ substream is mixed with methanol, while the second substream passes into the cleavage reactor with the DMS. The product streams of the two reactors are subsequently fed together to a product workup.

U.S. Pat. No. 2,831,031 discloses catalysts based on pyrophosphoric acid on titanium dioxide, over which dimethyl sulphide is converted to methyl mercaptan with a maximum selectivity of 97% at a conversion of 42%. U.S. Pat. No. 4,005,149 and JP 5246203 describe aluminum oxides doped with cobalt molybdate or tungsten sulphide, with which dimethyl sulphide conversions of, respectively, 41 and 88% and, respectively, selectivities of 92 and 93% for methyl mercaptan can be achieved. Further catalysts claimed in U.S. Pat. No. 4,313,006 are zeolites (X, Y, L) doped with sodium or potassium ions, with which maximum methyl mercaptan selectivities of 65% are achieved with a dimethyl sulphide conversion of 70%. JP 58159456 relates to aluminium oxides modified with phosphorus oxides and tungsten oxides, with which a maximum DMS cleavage conversion of 40% can be achieved. The $H_2S$/DMS ratio in the reactant gas is 2 to 28 in the above mentioned applications. Preference is given to pursuing a high $H_2S$/DMS ratio in order to achieve sufficiently high DMS cleavage conversions. U.S. Pat. No. 4,005,149 describes a process for catalytically cleaving organic sulphides with hydrogen sulphide in the presence of sulphactive catalysts. As a result of the addition of carbon disulphide to the reaction mixture, the overall conversion of sulphides to mercaptans can be increased. A disadvantage of this process is the use of toxic carbon disulphide in the process, which has to be separated again from the reaction products in a costly manner. Generally, in the cleavage of dialkyl sulphides to mercaptans with hydrogen sulphide, high selectivities for mercaptan and the maximum suppression of by-products are pursued. In contrast, the decomposition of (poly)sulphides to mercaptans, for example over aluminium oxides, without the addition of hydrogen sulphide, is characterized by comparatively low selectivities for methyl mercaptan and a broad spectrum of by-products. Mashkina et al., describe, for example, in *React. Kinet. Catal. Lett.*, Vol. 70, No. 1, 183-189, 2000, the decomposition of dimethyl disulphide to methyl mercaptan without $H_2S$ addition over acidic catalysts with maximum methyl mercaptan selectivities of 87%.

According to Koshelev, et al. [*React. Kinet. Catal.*, Vol. 27, No. 2, 387-391 (1985)] for the cleavage of dimethyl sulphide with hydrogen sulphide over γ-aluminium oxide, a maximum activity is achieved when the catalysts have a large number of aprotic Lewis acid sites and basic sites of moderate strength. The catalysts based on 3.5% $Na_2O/Al_2O_3$ described by Koshelev, et al. exhibit, at a DMS conversion of 9.5%, however, only maximum methyl mercaptan selectivities of 82%, while methyl mercaptan selectivities of 97% with a conversion of 38% are achieved over pure $γ-Al_2O_3$.

SUMMARY OF INVENTION

It is an object of the invention to provide an economically viable process, an apparatus and specific catalysts for preparing methyl mercaptan from dialkyl sulphides and/or dialkyl polysulphides and hydrogen sulphide.

The invention provides a process for continuously preparing alkyl mercaptans by reacting a reactant gas comprising dialkyl sulphides and/or dialkyl polysulphides with an at least molar excess of hydrogen sulphide at elevated temperature in the gas phase and a) in the presence of a catalyst based on or consisting of $Al_2O_3$, $SiO_2$, $TiO_2$, aluminosilicates, zeolites, bentonites or aluminas, which contain at least 1% by weight of alkali metal oxide, b) in a reactor which comprises at least n=2 separate catalyst zones, wherein c) the predominant portion or the total amount of the dialkyl sulphides and/or dialkyl polysulphides mentioned is introduced into the reactor into the first catalyst zone together with at least a portion of the total amount of the hydrogen sulphide used, and d) the remaining amount of the hydrogen sulphide and of the dialkyl sulphides and/or dialkyl polysulphides is metered in between the catalyst zones.

Alkyl means $C_1$ to $C_5$-alkyl, especially methyl. The polysulphides have generally 2 to 6 sulphur atoms.

The process is preferably performed continuously.

DETAILED DESCRIPTION OF INVENTION

Preferred examples of dialkyl sulphides and dialkyl polysulphides which are reacted in accordance with the invention with hydrogen sulphide to give alkyl mercaptan are dimethyl sulphide, dimethyl disulphide, dimethyl trisulphide, dimethyl tetrasulphide and dithiapentanes. These (poly)sulphides may be metered into the process alone or in a mixture with dimethyl sulphide. It is also possible to meter alkyl ether compounds, for example dimethyl ether, to the reactant gas, said alkyl ether compounds being reacted with hydrogen sulphide to give methyl mercaptan.

Equation (1) illustrates, using the example of the cleavage of dimethyl sulphide, that the reaction can be performed without formation of by-products. The aim of the invention is to perform the conversion to methyl mercaptan with a selectivity for the reaction product of greater than 98%. The formation of further by-products, for example carbon disulphide, should as far as possible be suppressed.

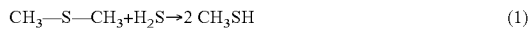

$$CH_3\text{—}S\text{—}CH_3 + H_2S \rightarrow 2\ CH_3SH \qquad (1)$$

Caused by the low exothermicity of the cleavage reaction, the preheated reactant gas mixture which comprises hydrogen sulphide and dialkyl (poly)sulphides can be converted to methyl mercaptan in an adiabatic reactor. The reactant gas mixture may also comprise dialkyl ethers or diaryl ethers, especially dimethyl ether.

The molar ratios of hydrogen sulphide and the total amount of dialkyl sulphide and dialkyl polysulphide range from 3:1 to 25:1, preferably 5:1 to 25:1, especially 10:1 to 25:1.

The reaction is preferably performed in a reactor in which at least 2, especially 2 to 25, catalyst zones are connected in series. The catalyst zones may be configured, for example, as fixed beds or tube bundles filled with catalyst. Optionally, it is also possible for a plurality of individual apparatuses of this type to be connected in series. The reactant mixture comprising gaseous or liquid dialkyl sulphides and/or dialkyl polysulphides, hydrogen sulphide and optionally further components is metered into the reactor in such a manner that preferably the total amount of dialkyl (poly)sulphides, upstream of the first catalyst zone, is added with a portion which corresponds to at least the nth part of the total amount of hydrogen sulphide, while the remaining amount of hydrogen sulphide is metered in between the catalyst zones. Optionally, it is also possible to add the total amount of hydrogen sulphide upstream of the first catalyst zone.

The product gas mixture can be separated by various known processes. A particularly advantageous separation is described in EP 0850923 B1, (U.S. Pat. No. 5,866,721). Unconverted dialkyl sulphide or dialkyl polysulphide is recycled into the reactor.

Figure 1:
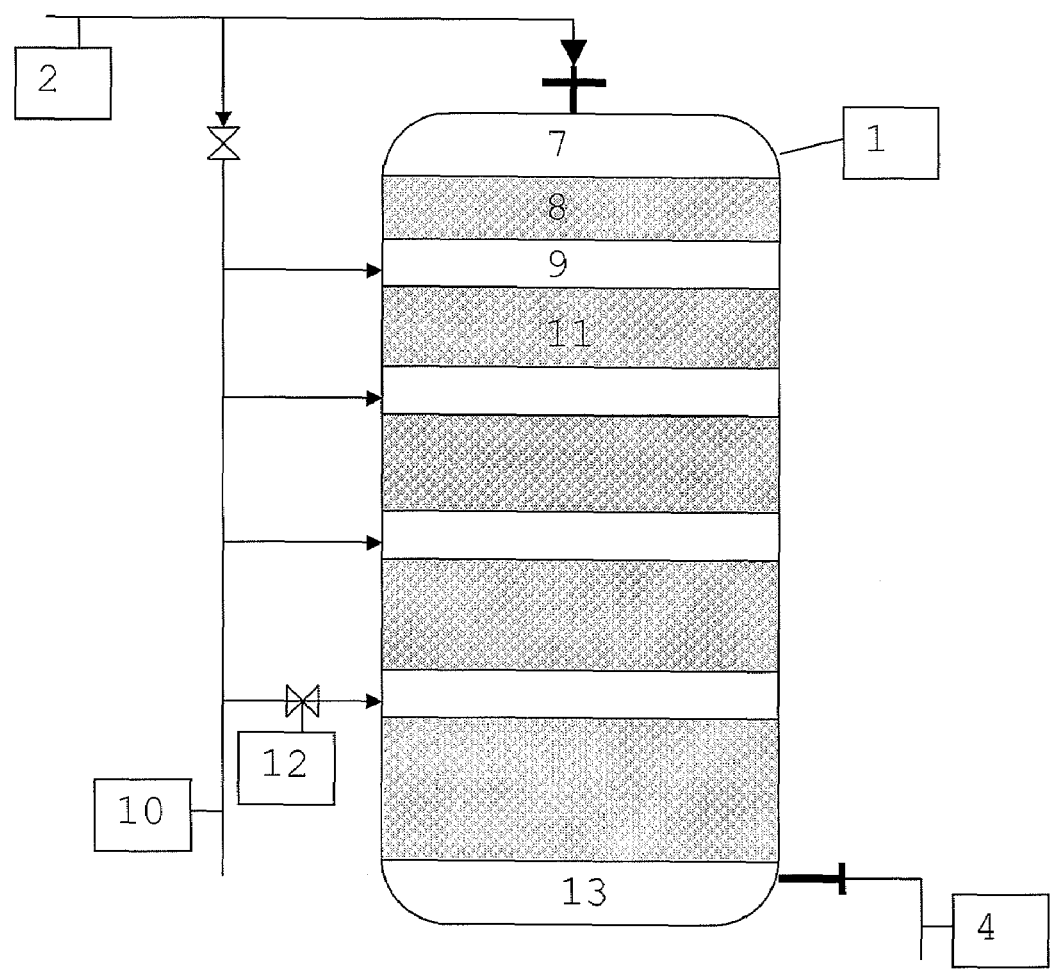
FIG. 1 shows one embodiment of the reactor according to the present invention.

FIG. 1 shows the preferred embodiment of the reaction apparatus for cleaving dialkyl (poly)sulphides to mercaptans. The gas comprising these compounds is referred to as reactant gas or reactant mixture and stems preferably from processes for preparing methyl mercaptan from hydrogen sulphide and methanol. In the reactor 1, n (n=2-25) catalyst zones which consist of a distributor chamber and a catalyst bed are accommodated. Preference is given to using 3-10 catalyst zones. The reactant mixture 2 comprising the alkyl (poly)sulphides mentioned enters the first catalyst bed 8 through the distributor chamber 7. This first catalyst bed is optionally, in flow direction of the reactant gas, covered first with a bed of inert materials. For example, aluminium oxide spheres or ceramic Raschig rings may be used as inert materials. Downstream of the inert bed is disposed the catalyst bed. After leaving the first stage, the gas mixture is enriched in the distributor chamber 9 with hydrogen sulphide 10 or optionally the reactant mixture 2. The gas mixture subsequently flows out of the distributor chamber 9 into the second catalyst bed 11, and devices in the distributor chamber 9 ensure turbulent flow and complete mixing of the reactants which is distributed uniformly over the entire area of the second catalyst bed. The supply of hydrogen sulphide or optionally the reactant gas mixture is effected analogously at n−1, preferably (where n>2) at n−2, injection points between the downstream catalyst beds of the apparatus. Optionally, it is possible to dispense with a supply of hydrogen sulphide or reactant gas mixture upstream of the last catalyst bed at injection point 12 in order to obtain full conversion in the reaction. The last catalyst zone may optionally also be configured longer than the other zones in order to enable full conversion.

The process is also characterized in that the reactant gas contains optionally at least 0.1% by volume, preferably 0.1 to 10% by volume, especially 1 to 10% by volume, of hydrogen based on the total amount. These measures suppress the formation of oligomers and polymers. In addition, further secondary components, for example nitrogen, water, carbon monoxide, carbon dioxide, carbonyl sulphide or dialkyl ether, may be present in the reactant gas.

The dialkyl (poly)sulphides are converted to mercaptans preferably over catalysts comprising alkali metal oxides at a temperature of 100 to 600° C., preferably 150 to 450° C., especially 300 to 430° C., and a pressure of 1.5 to 50 bar, preferably 8 to 40 bar. The catalyst supports used may be silicates, titanium oxides, zeolites, aluminas, aluminium oxides and preferably γ-aluminium oxides. The supports have preferably been modified with alkali metal oxides such that the Lewis acidity, compared to the unmodified catalyst support, is reduced in a controlled manner while simultaneously increasing the Lewis basicity. Preference is given to using γ-aluminium oxides containing 1-50% by weight, preferably 2 to 20% by weight, of alkali metal oxide as catalysts. Preference is given to using γ-aluminium oxides containing caesium oxide or rubidium oxide in the process according to the invention as catalysts. The catalysts are prepared, for example, by means of the impregnation of the catalyst support with suitable alkali metal salts, which are converted to the corresponding oxides by thermal decomposition. Preference is given to using alkali metal nitrates, carbonates or the alkali metal salts of carboxylic acids. The catalysts are subsequently dried and optionally calcined at temperatures of 50 to 600° C.

In a particular embodiment, the catalyst comprises oxidic compounds of one or more transition metals of atomic numbers 21 to 80, especially of V, Mn, Fe, Co, Ni, Cu, Zn, Zr, Nb, Mo or W.

These metals may also be present in the form of phosphates or pyrophosphates.

Before they are used for the first time, the catalysts are advantageously sulphidated in a hydrogen sulphide stream at a temperature of at least 100° C. for at least 1 h.

Example 1 shows, by way of example, the synthesis of the catalysts, while Example 2 describes the catalytic cleavage of dimethyl sulphide to methyl mercaptan.

EXAMPLE 1

Preparation of $M_2O$—$Al_2O_3$ (M=Li, Na, K, Rb, Cs) 49.66 g of $LiNO_3$ were dissolved in 300 ml of distilled water. The solution was heated to approx. 60° C., such that the salt had dissolved completely. 50 g of γ-aluminium oxide were added to the solution with stirring. The solution was subsequently stirred for approx. 60 min. The catalyst was stirred at a temperature of at least 60° C., optionally under reduced pressure, until the complete amount of liquid had been absorbed into the support. The catalyst was dried under air at approx. 120° C. overnight, and then calcined at 500° C. in an air stream for 3 h.

EXAMPLE 2

The DMS cleavage was studied in a temperature range of 100-500° C. and a pressure of 1.5-25 bar. The ratio of hydrogen sulphide to dimethyl sulphide (DMS) in the reactant gas was varied in the range of 1:1-25:1.

Figure 2:
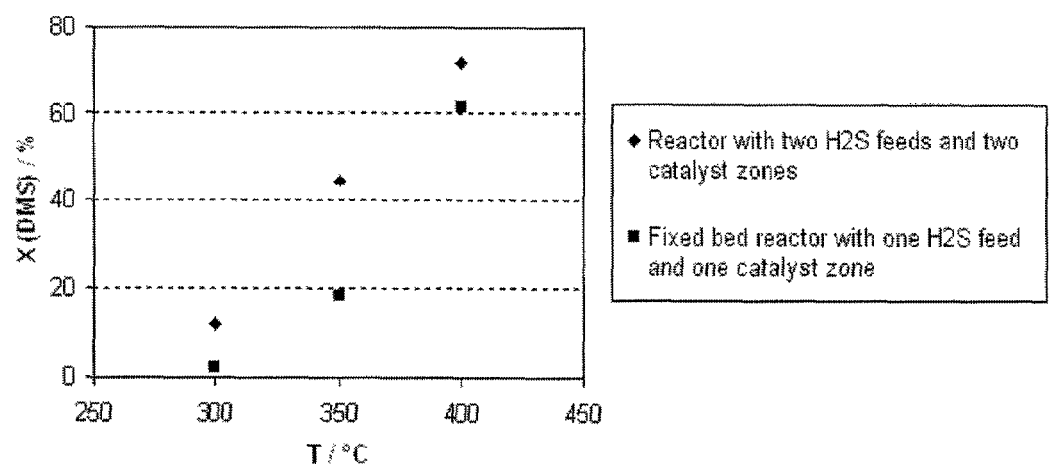
FIG. 2 shows the test results of the cleavage of dimethyl sulphide to methyl mercaptan in the presence of hydrogen sulphide over catalysts based on $Rb_2O$-$\gamma$-$Al_2O_3$, under the conditions of p=9 bar and $H_2S/DMS$=14/1.

Before the start of the reaction, the fresh catalysts were first sulphidated in the reactor at 350° C. for 2.5 h in a hydrogen sulphide stream. FIG. 2 shows, for $Rb_2O$—$Al_2O_3$ (spheralite) a comparison of the dimethyl sulphide cleavage conversions to methyl mercaptan as a function of the temperature with classical "overhead feeding" (fixed bed reactor with one catalyst zone) and in "two-zone operation", i.e. the $H_2S$ stream, similarly to a staged reactor with $H_2S$ intermediate feeding, was fed in upstream of the two catalyst zones. In both cases, the total $H_2S$ to DMS ratio was 14:1. The spatial velocities and gas loadings were identical in both cases. FIG. 2 illustrates that, in the inventive apparatus, over the catalysts which have been modified with alkali metal oxides and are claimed in this application, significantly higher DMS cleavage conversions can be achieved than in conventional "one-zone operation", for example in a conventional fixed bed reactor.

Figure 3:
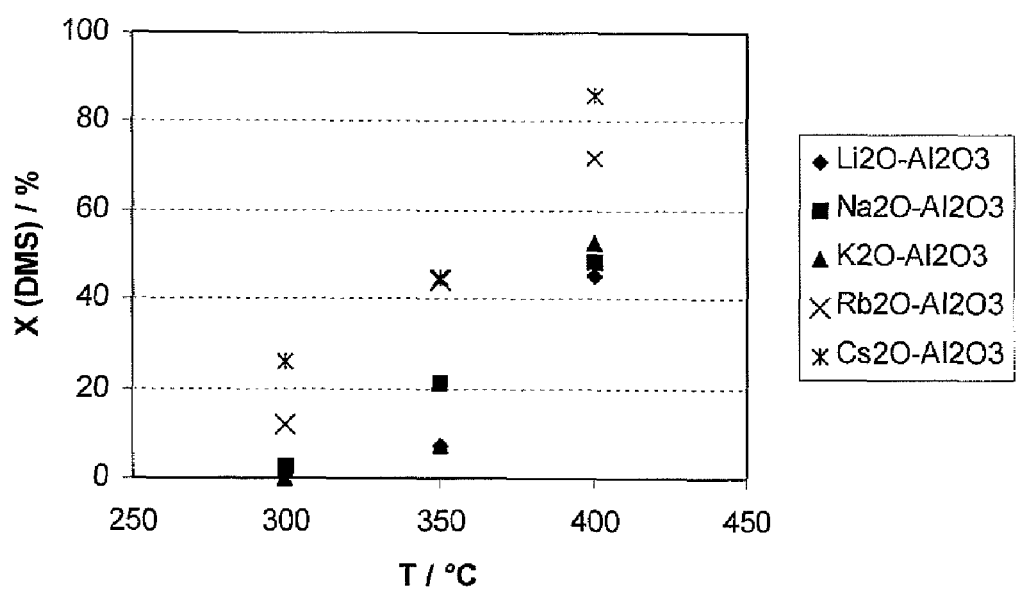
FIG. 3 shows the test results for the cleavage of dimethyl sulphide to methyl mercaptan in the presence of hydrogen sulphide in a reactor with two catalyst zones and $H_2S$ feeding upstream of the two catalyst zones in the presence of different catalysts.

FIG. 3 shows the positive influence of the increasing Lewis basicity of the catalysts in the inventive apparatus in "two-zone operation". With $Cs_2O$—$Al_2O_3$ catalysts, both in "one-zone" and "two-zone operation", significantly higher cleavage conversions were achieved than with catalysts based on $Li_2O$—$Al_2O_3$.

The overall selectivity for methyl mercaptan in all cases is 100%, i.e. no by-products were detected. Among other catalysts, $Cs_2O$—$Al_2O_3$, catalysts with different $Cs_2O$ loadings were synthesized (5-10% by weight). As is evident to those skilled in the art, modification with regard to γ-$Al_2O_3$.

source, performance of the impregnation, dispersion of the alkali metal oxides, porosity and BET surface area of the catalyst and performance of the catalyst conditioning or sulphidation can achieve even higher DMS cleavage conversions.

The economic viability of the overall process depends crucially on the product selectivity for methyl mercaptan based on the carbon source used (e.g. methanol). It is evident from the above that sulphides, for example dimethyl sulphide, can be converted to methyl mercaptan with high yields, which increases the overall selectivity of the preparation of methyl mercaptan. A particular advantage of the invention is that dialkyl (poly)sulphides, which would otherwise have to be incinerated as by-products or disposed of in a costly manner, can be utilized in a technically simple and inexpensive transformation as a raw material for methyl mercaptan. Moreover, in the process according to the invention, no toxic carbon disulphide or other by-products are formed.

The methyl mercaptan formed is removed from the product gas mixture together with the methyl mercaptan from the first process step (for example reaction of methanol with hydrogen sulphide), as explained in DE 1768826 (GB 1268842), in several distillation and scrubbing columns at temperatures between 10 and 140° C.

Further variations and modifications of the foregoing will be apparent to persons skilled in the art and are intended to be encompassed by the claims appended hereto.

The invention claimed is:

1. A process for continuously preparing an alkyl mercaptan comprising:
   reacting a reactant gas mixture containing a dialkyl sulphide and/or a dialkyl polysulphide with an at least molar excess of hydrogen sulphide at 100° C. to 600° C. in a gas phase and
   a) in the presence of a catalyst containing $Al_2O_3$, $SiO_2$, $TiO_2$, an aluminosilicate, a zeolite, a bentonite or an alumina, and at least 1% by weight of alkali metal oxide,
   b) in a reactor which includes "n" separate catalyst zones and "n" is at least 2, wherein
   c) the predominant portion or the total amount of the dialkyl sulphide and/or dialkyl polysulphide is introduced into the reactor upstream of a first catalyst zone together with at least a portion of the total amount of the hydrogen sulphide used, and
   d) a remaining amount of the hydrogen suiphide and of the dialkyl sulphide and/or dialkyl polysulphide is metered in between the catalyst zones,
   e) and the reactant gas mixture contains a dialkyl ether which reacts with hydrogen sulphide to give an alkyl mercaptan and hence increase the overall selectivity of the process.

2. The process according to claim 1, in which the reactant gas mixture additionally comprises dialkyl ethers.

3. The process according to claim 1, in which the total amount of the dialkyl sulphide and/or dialkyl polysulphide is introduced into the reactor into the first catalyst zone together with at least 1/n part of the hydrogen sulphide used.

4. The process according to claim 1, in which the catalyst is $\gamma$-$Al_2O_3$ which contains at least 1% by weight of an alkali metal oxide.

5. The process according to claim 1, in which the catalyst contains at least 1% by weight of an alkali metal oxide selected from the group of Cs or Rb.

6. The process according to claim 1, in which the catalyst is modified by a compound of a transition metal.

7. The process according to claim 1, where the catalyst zones of the reactor are configured as fixed beds, tube bundles or fluidized beds.

8. The process according to claim 1, in which a plurality of reactors are connected in series.

9. The process according to claim 1, in which the hydrogen sulphide is present in a molar ratio to the total amount of dialkyl sulphide and and/or dialkyl polysulphide in the range of 3:1 to 25:1.

10. The process according to claim 1, in which the reactant gas mixture comprises the dialkyl sulphide and/or the dialkyl polysulphide is obtained as a by-product in the preparation of alkyl mercaptan.

11. The process according to claim 1, wherein the reactant gas mixture contains at least 0.1% hydrogen.

12. The process according to claim 1, characterized in that wherein the catalyst, before being used for a first time, is sulphidated at a temperature of at least 100 °C. in a hydrogen suiphide stream for at least 1 hour.

13. The process according to claim 1, wherein the reacting is effected at a pressure of 1.5 to 50 bar.

14. The process according to claim 1, wherein the reacting is effected at a temperature of 300 to 430° C., and a pressure of 8 to 40 bar.

* * * * *